United States Patent [19]
Ding et al.

[11] Patent Number: 5,879,697
[45] Date of Patent: Mar. 9, 1999

[54] DRUG-RELEASING COATINGS FOR MEDICAL DEVICES

[76] Inventors: Ni Ding, 4365 Juneau La., Plymouth, Minn. 55446; Jennifer E. Raeder-Devens, 83 Cambridge St., St. Paul, Minn. 55105; Tuyethoa Thi Trinh, 2479 Hamline Ave. North, Roseville, Minn. 55113

[21] Appl. No.: 841,747

[22] Filed: Apr. 30, 1997

[51] Int. Cl.$^6$ .................................................. A61F 13/00
[52] U.S. Cl. ........................ 424/422; 424/423; 424/424; 604/891.1; 623/11
[58] Field of Search ................................ 424/422, 423, 424/424; 604/891.1; 623/11

[56] References Cited

U.S. PATENT DOCUMENTS

| | | | |
|---|---|---|---|
| 3,549,409 | 12/1970 | Dyck | 428/475.5 |
| 4,292,965 | 10/1981 | Nash et al. | |
| 4,442,133 | 4/1984 | Graco et al. | 427/2.25 |
| 4,613,665 | 9/1986 | Larm | 536/20 |
| 4,676,975 | 6/1987 | McGary et al. | 424/423 |
| 4,871,357 | 10/1989 | Hsu et al. | 604/266 |
| 4,872,867 | 10/1989 | Joh et al. | |
| 4,895,566 | 1/1990 | Lee | 604/266 |
| 5,061,738 | 10/1991 | Solomon et al. | 523/100 |
| 5,141,748 | 8/1992 | Rizzo | 424/425 |
| 5,167,960 | 12/1992 | Ito | 424/423 |
| 5,217,743 | 6/1993 | Farah | 427/2 |
| 5,356,433 | 10/1994 | Rowland | 623/11 |
| 5,380,299 | 1/1995 | Fearnot et al. | |
| 5,383,927 | 1/1995 | De Giocoechea et al. | 623/1 |
| 5,441,759 | 8/1995 | Crouther et al. | 427/2.3 |
| 5,447,724 | 9/1995 | Helmus et al. | 424/426 |
| 5,525,348 | 6/1996 | Whitbourne et al. | 424/423 |
| 5,545,208 | 8/1996 | Wolff et al. | |
| 5,716,981 | 2/1998 | Hunter et al. | |

OTHER PUBLICATIONS

Kim, et al., "Nontrhombogenic Polymers, Pharmaceutical Approaches," Amer. Soc. Artificial Internal Organs Journal, vol. 6, p. 76 (1983).

O'Neil et al., "The Use Of TDMAC–Heparin Shunt In The Closure Of A Calcified Patent Ductus Artetiosus," J. Cardiovas. Surg, 22 p. 569 (1981).

Chan, et al., "The Effect Of A TDMAC–Heparin Bonded Aortofemoral Shunt On Experimental Spinal Cord Injury," The American Surgeon, p. 607 (Nov. 1980).

Jozefowicz, et al., "Heparin–Containing And Heparin–Like Polymers," Polymer Science Tech. v.34: p. 41 (1981).

(List continued on next page.)

*Primary Examiner*—D. Gabrielle Brouillette

[57] ABSTRACT

The invention is directed to medical devices having a drug-releasing coating and methods for making such coated devices. The coating permits timed or prolonged pharmacological activity on the surface of medical devices through a reservoir concept. Specifically, the coating comprises at least two layers: an outer layer containing at least one drug-ionic surfactant complex overlying a reservoir layer containing a polymer and the drug which is substantially free of an ionic surfactant. Upon exposure to body tissue of a medical device covered with such coating, the ionically bound drug in the outer layer is released into body fluid or tissue. Following release of such bound drug, the ionic surfactant binding sites in the outer layer are left vacant. To maintain the pharmacological activity after delivery of the ionically bound drug, additional amounts of the drug are embedded or incorporated in the reservoir layer in a manner which allows the drug, which is substantially free of ionic surfactants, to complex with the vacant binding sites of the ionic surfactant of the outer layer. As a result, the surface of the medical device is enriched with the drug to provide sustained pharmacological activity to prevent the adverse reaction due to the presence of the medical device. The invention is further directed to medical devices with stabilized drug-releasing coatings. The coatings are stabilized by exposure to a low energy, relatively non-penetrating energy source, e.g., gas plasma or an electron beam energy source.

19 Claims, 1 Drawing Sheet coating w. and w/o TDMAC top coat

OTHER PUBLICATIONS

Gott, "Heparinized Shunts For Thoracic Vascular Operations," Gibbons's Surgery of the Chest, 3r ed. p. 942 (1976).

Ruggieri, et al., "Reduction Of Bacterial Adherence To Catheter Surface With Heparin," J. of Urology, vol. 138: p. 423 (Aug. 1987).

Chang, et al., "Experimental Evaluation Of A New Type Of Heparin–Bonded Polyurethane," ASAIO Trans. v.37:(3) p. M201–2 (Jul.–Sep. 1991).

Mansoor Amiji and Kinam Park, "Surface Modification Of Polymeric Biomaterials With Poly(Ethylene Oxide), Albumin, And Heparin For Reduced Thrombogenicity", Purdue University, School of Pharmacy, 1992.

DRUG-RELEASING COATINGS FOR MEDICAL DEVICES

FIELD OF THE INVENTION

This invention relates generally to drug-releasing coatings for medical devices which are inserted or implanted into the body. More particularly, the invention is directed to medical devices having a drug-releasing coating comprising at least two layers: a reservoir layer and an outer layer comprising an ionic surfactant complexed to a biologically active material. Furthermore, the invention is directed to methods of stabilizing ionically complexed drug coatings.

BACKGROUND OF THE INVENTION

Exposure to a medical device which is implanted or inserted into the body of a patient can cause the body tissue to exhibit adverse physiological reactions. For instance, the insertion or implantation of certain catheters or stents can lead to the formation of emboli or clots in blood vessels. Similarly, the implantation of urinary catheters can cause infections, particularly in the urinary tract. Other adverse reactions to medical devices include cell proliferation which can lead to hyperplasia, occlusion of blood vessels, platelet aggregation, rejection of artificial organs, and calcification.

To reduce such adverse effects, pharmaceuticals, such as anticoagulants and antibiotics, have been administered in or on medical devices. A number of methods for delivering the drug(s) through implantation or insertion of the medical device involve covalently bonding the drug to the medical device, i.e, substrate. For example, U.S. Pat. No. 4,613,665 to Larm describes the coupling of heparin with reactive aldehyde groups to an animated surface by reductive amination.

Also, U.S. Pat. Nos. 5,112,457 and 5,455,040 to Marchant disclose the use of a similar approach to end-bind heparin on modified substrates. The substrate modification consists of depositing a film of plasma polymerized N-vinyl-2-pyrrolidone and attaching a spacer (e.g. PEG) on the film. The end group of the spacer is a primary amine, which can be bonded to aldehyde-ended heparin through reductive amination.

However, the covalent bonding approaches are limited. Only the surfaces of covalently bound coatings provide pharmaceutical activity, resulting in insufficient pharmaceutical activity at the treatment site. Furthermore, the drug loading of the medical device is limited by its surface area since the drug must be attached to the surface of the coating.

Pharmaceuticals have also been applied to medical devices by covering the surface with a coating containing them. A number of these coatings involve the ionic binding of the drug to the substrate. These approaches generally comprise the deposition of water-insoluble complexes of drugs and ionic surfactants on the surfaces of medical devices.

Illustrative of such approaches is the use of tridodecylmethylammonium chloride (TDMAC) or benzalkonium chloride, positively charged or cationic surfactants which are ionically complexed to negatively charged molecules of pharmaceuticals. Typical examples include tridodecylmethylammonium (TDMA)-heparin and TDMA-antibiotics. The former complex has been widely used as coatings on catheters, shunts and other blood contacting devices. The TDMA-heparin treatment can be applied to numerous biomedical materials including polyurethane, silicone, polypropylene, polycarbonate, PVC, metals and glass. TDMA-antibiotics have been used to reduce infections related to implants, urinary catheters and the like.

Although these ionic complex approaches allow numerous biomaterials to be coated with drugs without elaborate surface modification, they suffer from certain disadvantages. Notably, the ionically complexed drug tends to be quickly released from the medical device upon contact with body fluids so that its activity at the point of implantation or insertion diminishes rapidly. Attempts have been made to stabilize these coatings by crosslinking the ionically complexed drugs with glutaraldehyde or other bifunctional reagents. Recently, U.S. Pat. No. 5,441,759 to Crouther et al. discloses that exposure to gamma radiation and post-exposure heat treatment can strengthen the complex of TDMA-heparin to PVC surfaces. However, these attempts have demonstrated limited improvement. Specifically, such exposure to gamma radiation has been demonstrated in certain cases to have adverse effects upon the device. For instance, certain polymers degrade, crosslink, or change color upon exposure to gamma radiation, which may result in a loss of mechanical properties.

Also, attempts have been made to prolong the activity of ionically complexed drugs by mixing polymers with the drug-surfactant complexes to form coating compositions. See e.g. U.S. Pat. No. 5,525,348 to Whitbourne et al., U.S. Pat. No. 5,061,738 to Solomon et al., and U.S. Pat. No. 4,670,975 to McGary et al. However, inclusion of a polymer has not shown significant increase in prolonging activity. Moreover by employing drugs which are ionically complexed to surfactant, the amount of drug that can be loaded into the coating is limited since in general the drug constitutes only 20–50% of the complex. Thus the incorporation of the surfactant restricts the amount of drug that can be placed into the coatings of the medical device.

Hence, there is a need for stable coatings for medical devices which permit sufficient release of drugs at a certain rate or over a desired period of time into body fluid while maintaining high pharmaceutical activity on the surface. Therefore it is an object of the invention to provide such a coating for timed release of the incorporated drugs.

It is also an object of this invention to provide a drug-containing medical device which allows sustained delivery of the pharmaceutical or sufficient pharmaceutical activity at or near the coated surfaces of the devices.

Also, it is an object of the invention to provide medical devices with stabilized ionically complexed drug coatings and methods for making such devices.

Additionally, it is an object of the invention to provide a drug-releasing coating which adequately adheres to a medical device to allow the timed or prolonged application of the drug to body tissue.

It is a further object of the invention to provide methods for making a drug-releasing medical device which permit timed-delivery or long-term delivery of the drug.

SUMMARY OF THE INVENTION

These and other objects are accomplished by the present invention. To achieve these objectives, we have developed a coating which permits timed or prolonged pharmacological activity on the surface of medical devices through a reservoir concept. Specifically, the coating comprises at least two layers: an outer layer containing at least one drug-ionic surfactant complex overlying a reservoir layer or tie layer containing a polymer and the drug which is substantially free of an ionic surfactant. Upon exposure to body tissue of a medical device covered with such coating, the ionically complexed drug in the outer layer is released into body fluid or tissue. Following release of such complexed drug, the ionic surfactant complex sites in the outer layer are left vacant. To maintain the pharmacological activity after delivery of the ionically complexed drug, additional amounts of the drug are embedded or incorporated in the reservoir layer in a manner which allows the drug, which is substantially free of ionic surfactants, to form a complex with the vacant complex sites of the ionic surfactant of the outer layer. As a result, the surface of the medical device is enriched with the drug to provide sustained pharmacological activity to prevent the adverse reaction due to the presence of the medical device. In use, some of the drug which is embedded or incorporated in the reservoir layer can complex to vacant complex sites in the outer layer, while some of the drug, which is embedded or incorporated in the reservoir layer can freely elute into the body fluid.

To further achieve the objectives, we have also devised a method to stabilize drug-releasing coatings comprising ionically-complexed drugs. By exposing the coated device to a low energy, relatively non-penetrating energy source such as gas plasma, electron beam energy, or corona discharge, the coating is stabilized to permit timed or long-term delivery of the drug. Preferably, the coated device is first exposed to heat to secure the drug coating prior to exposure to the energy source. Moreover, application of this method of stabilization is not limited to the reservoir layer coating described above. It can be used with other coatings such as one comprising a first layer containing a polymer which is overlaid with a second layer containing a polymer and a drug-ionic surfactant complex.

The coatings of the invention can be used for a variety of medical devices such as catheters, shunts, stents (e.g. self expandable or balloon expandable vascular or non-vascular stents), heart valves, grafts, and artificial organs or prostheses. The coatings may be used with polymeric, metallic or ceramic surfaces.

The polymers suitable for use in the invention, such as in forming the reservoir layer, should be ones that are biocompatible and avoid irritation of body tissue. Preferably for medical devices which undergo mechanical challenges, elastomeric polymers such as silicones, polyurethanes, thermoplastic elastomers, ethylene vinyl acetate copolymers, polyolefin elastomers, and EPDM rubbers may be used. For medical devices which do not undergo mechanical challenge, bioabsorbable polymers may be used. Such bioabsorbable polymers included polylactic acid, polyglycolic acid, polycaprolactone, polylactic acid-polyethylene oxide copolymers, cellulose and the like.

The biologically active material suitable for the invention can be in a particulate form. Average particle size can be 1 to 100 microns. The biologically active materials useful for the invention include glucocorticoids, heparin, hirudin, angiopeptin, aspirin, growth factors, oligonucleotides, anti-platelet agents, anti-coagulant agents, antimitotic agents, antioxidants, antimetabolite agents, anti-inflammatory agents, anti-hypertensives, and antibiotics such as penicillin. The reservoir layer can contain 0.1 to 90 weight % of the biologically active material, preferably 10–45 weight %, and can have a thickness ranging from about 5 to about 1000 microns. Preferably, the reservoir layer ranges from about 15 to about 50 or 200 microns thick.

For the outer layer, suitable ionic surfactants comprise tridodecylmehtylammonium chloride, or benzalkonium chloride. The outer layer can have a thickness ranging from about 0.1 to about 10 microns; preferably, the outer layer is about 1 to about 5 microns thick.

In accordance with the present invention, negatively charged drugs contact positively charged surfactants to form a complex. Once the complex is formed, the solubility of the drug in body fluid is significantly reduced. Thus, the release rate of the drug in the body fluid is decreased. Similarly, positively charged drugs can form complexes with negatively charged surfactants to achieve similar results.

The complexes formed according to the present invention will result primarily from ionic interactions between negatively charged drugs and positively charged surfactants or positively charged drugs and negatively charged surfactants. However, certain secondary forces may also exist to contribute to the formation or maintenance of the complexes, such as hydrogen bonding, dipole-dipole interaction, charge-dipole interaction, and the complexes of the initial outer layer may be identical or similar to the complexes subsequently formed by the biologically active material of the reservoir. However, the complexes may differ. For instance an initial complex may have a higher density of charge-charge interaction between a pharmaceutical agent and a surfactant as compared to subsequent complexes formed by biologically active material of the reservoir and the surfactant.

To prepare the reservoir coatings of the present invention, the reservoir layer is first formed on the medical device. The drug is incorporated by dissolving or suspending it in a polymer and solvent composition. A crosslinking agent can optionally be added to the solution or suspension. The reservoir layer composition is then applied to a surface of the medical device by methods such as, but not limited to, spraying or dipping. The reservoir layer can then be optionally heat cured. The outer layer is prepared by dissolving a drug-ionic surfactant complex in a solvent or a mixture of solvents which are swellable to the polymer(s) in the reservoir layer. The outer layer composition is applied over the reservoir layer to form the outer layer. Some of the complex will penetrate into the polymeric reservoir coat.

To make the stabilized coatings of the present invention, after the first layer of the coating is applied to the device (if the coating comprises more than one layer), the device can be heat treated and then exposed to a low energy, relatively non-penetrating energy source to further cure the layer. Optionally, the device can be heat treated without exposure to the energy source or exposed to the energy source without heat treatment, additional layers can then be applied. The device can then again be heat treated and/or exposed to the energy source. The outer layer of the device may optionally be heat treated, but should be exposed to the energy source in any event r- for stabilization.

DESCRIPTION OF THE PREFERRED EMBODIMENTS

Figure 1:
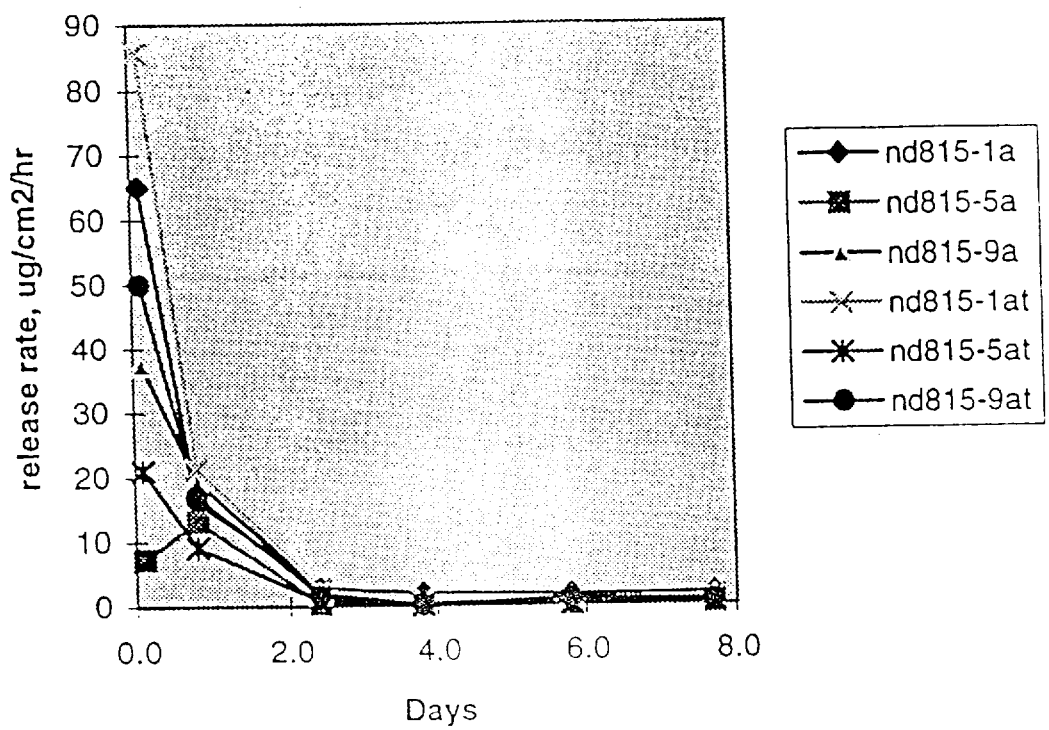
FIG. 1 is a plot showing the release rate of heparin for stents with the coatings made according to Example 1.

The medical devices suitable for the present invention include but are not limited to catheters, implantable vascular access ports, blood storage bags, vascular stents, blood tubing, central venous catheters, arterial catheters, vascular grafts, intraaortic balloon pumps, heart valves, cardiovascular sutures, total artificial heart and ventricular assist pump, extracorporeal devices such as blood oxygenators, blood filters, hemodialysis units, hemoperfusion units, plasmapheresis units, hybrid artificial organs such as pancreas or liver and artificial lungs.

Devices which are particularly suitable include vascular stents such as self-expanding stents and balloon expandable stents. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 4,733,665 issued to Palmaz, U.S. Pat. No. 4,800,882 issued to Gianturco and U.S. Pat. No. 4,886,062 issued to Wiktor. Similarly, urinary implants such as drainage catheters are also particularly appropriate for the invention.

The surfaces of the medical devices may be formed from polymeric, metallic and/or ceramic materials. Suitable polymeric materials include without limitation polyurethane and its copolymers, silicone and its copolymers, ethylene vinyl-acetate, thermoplastic elastomers, polyvinyl chloride, polyolefins, cellulosics, polyamides, polyesters, polysulfones, polytetrafluorethylenes, polycarbonates, acrylonitrile butadiene styrene copolymers, acrylics, polylactic acid, polyglycolic acid, polycaprolactone, polylactic acid-polyethylene oxide copolymers, cellulose, collagens, and chitins.

Metallic materials include metals and alloys based on titanium (such as nitinol, nickel titanium alloys, thermo-memory alloy materials), stainless steel, tantalum, nickel-chrome, or cobalt-chromium (such as Elgiloy® and Phynox®). Metallic materials also include clad composite filaments, Such as those disclosed in WO 94/16646. Examples of ceramic materials include ceramics of alumina and glass-ceramics such as Macor®.

As described above, the reservoir layer composition comprises a polymer and a biologically active material. Optionally a cross-linking agent may be included. The following is a more detailed description of suitable materials or agents and methods useful in producing the reservoir layer of the coatings of the invention.

The polymer(s) useful for forming the reservoir layer should be ones that are biocompatible and avoids irritation to body tissue. Preferably the polymers are biostable ones, such as polyurethanes, silicones, and polyesters. Other polymers which can be used include ones that can be dissolved and cured or polymerized on the medical device or polymers having relatively low melting points that can be blended with therapeutic agents. Suitable polymers include polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate; copolymers of vinyl monomers, copolymers of vinyl monomers and olefins such as ethylene-methyl methacrylate copolymers, acrylonitrile-styrene copolymers, ABS resins, ethylene-vinyl acetate copolymers, polyamides such as Nylon 66 and polycaprolactone, alkyd resins, polycarbonates, polyoxymethylenes, polyimides, polyethers, epoxy resins, polyurethanes, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, and polylactic acid-polyethylene oxide copolymers.

More preferably for medical devices which undergo mechanical challenges, e.g. expansion and contraction, the polymers are selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. Because of the elastic nature of these polymers, the coating better adheres to the surface of the medical device when the device is subjected to forces or stress.

Furthermore, although the invention can be practiced by using a single type of polymer to form the reservoir layer, various combinations of polymers can be employed. The appropriate mixture of polymers can be coordinated with biologically active materials of interest to produce desired effects when coated on a medical device in accordance with the invention.

The drugs or biologically active materials which can be used in the invention can be any therapeutic substances such as those which reduce or prevent adverse physiological reactions from exposing body tissue to the medical device. The drugs incorporated into the reservoir layer should be substantially free of ionic surfactants. The drugs can be of various physical states, e.g., molecular distribution, crystal forms or cluster forms. A combination of suitable pharmaceuticals can be incorporated into the reservoir layer.

Suitable therapeutic substances include glucocorticoids (e.g. dexamethasone, betamethasone), heparin, hirudin, angiopeptin, aspirin, growth factors, oligonucleotides, and, more generally, antiplatelet agents, anti-coagulant agents, antimitotic agents, antioxidants, antimetabolite agents, and anti-inflammatory agents could be used. Antiplatelet agents can include drugs such as aspirin and dipyridamole. Aspirin is classified as an analgesic, antipyretic, anti-inflammatory and antiplatelet drug. Dipyridamole is a drug similar to aspirin in that it has anti-platelet characteristics. Dipyridamole is also classified as a coronary vasodilator. Anti-coagulant agents can include drugs such as heparin, protamine, hirudin and tick anticoagulant protein. Antimitotic agents and antimetabolite agents can include drugs such as methotrexate, azathioprine, vincristine, vinblastine, 5-fluorouracil, adriamycin and mutamycin. Antibiotic agents can include penicillin, cefoxitin, oxacillin, tobramycin, and gentamycin.

The biologically active agents can be incorporated by dissolving or suspending them in the polymer and solvent of the reservoir layer composition. If the drugs are suspended in the solution, they should be dispersed as fine particles ranging from 1–100 microns in average particle size. Alternatively, if a polymer having a relatively low melting point is used, the polymer and biologically active agent can be blended in the molten stage (such as by casting or coextrusion) if the biologically active agent does not degrade at the molten temperature. The ratio of reservoir layer thickness to average particle diameter is preferably greater than about 3, and more preferably greater than about 5.

The concentration or loading of the biologically active material in the reservoir layer may be varied according to the therapeutic effects desired. Also, the loading, in terms of the ratio of pharmaceutical to polymer in the reservoir layer, will depend upon the efficacy of the polymer in securing the pharmaceutical onto the medical device and the rate at which the coating is to release the pharmaceutical to the body tissue. Generally, the reservoir layer may contain 0.1–90% by weight or preferably 10–45% by weight of the biologically active material. Most preferably, 25–40% by weight of the drug should be incorporated in the reservoir layer.

The reservoir layer will generally be prepared to be substantially free of any ionic surfactant. However, small amounts may become present, especially at an interface between an outer layer and a reservoir layer. For instance, small amounts of ionic surfactant may become present as a result of penetration during an outer layer spraying process or due to migration from the outer layer during shelf storage. The reservoir layer, apart from the interface with the outer layer, will preferably have less than 0.5 weight percent complex, more preferably less than 0.4 weight percent complex.

Solvents suitable for forming the reservoir layer composition are ones which can dissolve the polymer into solution and do not alter or adversely impact the therapeutic properties of the biologically active material employed. Examples of useful solvents for silicone include tetrahydrofuran (THF), chloroform and dichloromethane.

To enhance the stability of the reservoir layer and the timed or long-term release of the pharmaceuticals, crosslinkers may be incorporated into the reservoir layer. For instance, hydridosilane may be used as a crosslinking agent for silicone.

The reservoir layer composition is generally prepared by adding micronized drug particles into a selected amount of polymer. Solvent and optional crosslinking agent are then added to this mixture which is then stirred until it is homogeneous. Depending on the nature of the biologically active material and the solvent and polymers used, the mixture need not be a solution. The drug particles need not be dissolved into the mixture but may be suspended therein.

The mixture is then applied to a surface of the medical device. The reservoir layer composition may be applied by dipping the medical device into the composition or by spraying the composition onto the device. The thickness of the reservoir layer formed may range from about 5 microns to about 100 microns and preferably from about 15 microns to about 50 microns.

Since different coating thicknesses can be readily achieved by adjusting the number of spray cycles, spray coating the medical device with the reservoir layer is preferred. Typically, an airbrush such as a Badger Model 150 (supplied with a source of pressurized air) can be used to coat the device. If a significant amount of surface area is to be coated, it may be preferable to place the device in a rotating fixture to facilitate the coverage of the device's surface. For example, to coat the entire surface of a vascular stent, the ends of the device are fastened to a rotating fixture by resilient retainers, such as alligator clips. The stent is rotated in a substantially horizontal plane around its axis. The spray nozzle of the airbrush is typically placed 2–4 inches from the device.

The thickness of the reservoir coat can be adjusted by the speed of rotation and the flow rate of the spray nozzle. The speed of rotation is usually adjusted at about 30–50 rpm, typically at about 40 rpm. The flow rate of the spray nozzle, which can range from 4–10 ml coating per minute may also be adjusted. Usually, a number of spraycoats will be required to achieve the desired thickness of a reservoir layer. If a non-spray process is utilized, such as dip coating, casting or coextrusion, then one coat may be sufficient.

Moreover, several reservoir layers of different compositions may be used so that more than one drug and/or polymer may be incorporated into the underlying coat. The placement of the different layers may be determined by the diffusion or elution rates of the drugs involved as well as the desired rate of delivering the drug to the body tissue.

After application of the reservoir layer, the polymer can be cured to produce a polymer matrix containing the biologically active material and the solvent evaporated. Certain polymers, such as silicone, can be cured at relatively low temperatures, (e.g. room temperature) in what is known as a room temperature vulcanization (RTV) process. More typically, the curing/evaporation process involves higher temperatures so that the coated device is heated in an oven. Typically, the heating occurs at approximately 90° C. or higher for approximately 1 to 16 hours when silicone is used. For certain coatings such as ones containing dexamethasone, the heating may occur at temperatures as high as 150° C. The time and temperature of heating will of course vary with the particular polymer, drugs, solvents and/or crosslinkers used. One of skill in the art is aware of the necessary adjustments to these parameters. Also, the devices may be cured after the outer layer has been applied.

The outer layer containing the ionic surfactant-drug complex is preferably prepared by dissolving the complex in a solvent or a mixture of solvents, however, it can also be prepared by blending the ionic surfactant drug complex with polymer(s) or polymer(s)/solvent mixtures. Suitable drugs have been described above. Appropriate ionic surfactants include quaternary ammonium compounds such as one of the following: benzalkonium chloride, tridodecylmethylammonium chloride (TDMAC), cetylpyridinium chloride, benzyldimethylstearylammonium chloride, benzylcetyl dimethyl ammonium chloride. An additional example of an appropriate ionic surfactant includes a polymeric surfactant, such as a quaternary ammonium salt of acrylate polymer including 2-(trimethyl amine)-ethyl methacrylate bromide, or a quaternary ammonium salt of cellulose such as JR400 and QUATRISOFT manufactured by Union Carbide. Preferably, the ionic surfactant comprises TDMA.

The surfactant-drug complex can either be purchased on the open market or made in the laboratory. For instance, benzalkonium chloride is made and sold by ALDRICH. TDMA-heparin is made and sold by STS POLYMERS. The skilled artisan is aware of methods for making surfactant-drug complexes.

The concentration or loading of biologically active material in the outer layer may be varied according to the therapeutic effects desired. Generally, the outer layer may contain 10–100% by weight or preferably 30–100% by weight of the complex of the biologically active material. Most preferably, 45–100% by weight of the drug complex should be incorporated in the outer layer.

The solvent(s) used to dissolve the complex should be swellable to the reservoir layer polymers. In other words, the solvent(s) should allow the outer layer composition to somewhat mix with the reservoir layer at the interface of the two layers. Hence, if possible, the solvent used to prepare the outer layer should preferably be the same as that used to make the reservoir layer.

The outer layer composition is then applied to the medical device. The composition can be applied by such methods as dipping, casting, extruding or spray coating to form a layer in which some of the drug-surfactant complex will penetrate into the very top of matrix polymer of the reservoir layer. As with the reservoir layer, spray coating the outer layer onto the medical device is preferred since it permits the thickness of the coating to be readily adjusted. The thickness of the outer layer can range from about 0.1 to about 10 microns. Preferably, this layer is about 1 to about 5 microns thick. When spray coating, 1–2 spray cycles are preferred, however additional cycles may be applied depending upon the coating thickness desired.

The coating thickness ratio of the outer layer to the reservoir layer may vary from about 1:2 to 1:100 and is preferably in the range of from about 1:10 to 1:25.

The release rate and release profile of the device can be affected by the thickness of the outer layer as well as the concentration of the ionically bound pharmaceutical in that layer. If a greater amount of the biologically active material is to be delivered initially, thinner outer layers should be used.

To prepare the stabilized coatings of this invention, the medical devices are exposed to a low energy, relatively non-penetrating energy source such as gas plasma, electron beam energy, or corona discharge after they are covered with at least a layer of a drug-releasing coating. The gas used in the gas plasma treatment can be preferably argon or other gases such as nitrogen, helium or hydrogen. Preferably the coated device is first heat cured at 40° C. to 150° C. prior to the exposure to the energy source for 30 seconds to 30 minutes. Relatively penetrating energy sources such as gamma radiation should be avoided.

Also, such treatment can be applied to the device prior to completing the application of the entire coating. For example, after the device is coated with a layer of the coating it can be heated and exposed to the low energy, relatively non-penetrating energy source. The treatment can be repeated after other layers have been applied. In addition this method of stabilization can be applied to coatings other than the reservoir coating described above. Specifically, the method is applicable to a coating having a first layer comprising a polymer and a second layer comprising a polymer and an ionically complexed drug. The method is also applicable to a single coating which contains an ionically complexed drug. The polymers and drug complexes described above are suitable for preparing such a coating.

In one suitable method, the medical devices are placed in a chamber of a plasma surface treatment system such as a Plasma Science 350 (Himont/Plasma Science, Foster City, Calif.). The system is equipped with a reactor chamber and RF solid-state generator operating at 13.56 mHz and from 0–500 watts power output and being equipped with a microprocessor controlled system and a complete vacuum pump package. The reaction chamber contains an unimpeded work volume of 16.75 inches (42.55 cm) by 13.5 inches (34.3 cm) by 17.5 inches (44.45 cm) in depth.

In the plasma process, coated medical devices are placed in a reactor chamber and the system is purged with nitrogen and a vacuum applied to 20–50 mTorr. Thereafter, inert gas (argon, helium or mixture of them) is admitted to the reaction chamber for the plasma treatment. A highly preferred method of operation consists of using argon gas, operating at a power range from 200 to 400 watts, a flow rate of 150–650 standard ml per minute, which is equivalent to 100–450 mTorr, and an exposure time from about 30 seconds to about 5 minutes. The devices can be removed immediately after the plasma treatment or remain in the argon atmosphere for an additional period of time, typically five minutes.

Following stabilization, the ionic surfactant drug complex of the outer layer will generally be molecularly distributed or in particle form.

Moreover, after the medical devices are coated, they should be sterilized. Methods of sterilization are known in the art. For example, the devices can be sterilized by exposure to gamma radiation at 2.5–3.5 Mrad or by exposure to ethylene oxide. For sterilization, exposure to gamma radiation is a preferred method, particularly for heparin containing coatings. However, for certain medical devices which undergo mechanical challenges, such as expandable vascular stents, it has been found that subjecting such coated devices to gamma radiation sterilization may reduce their ability to expand. To avoid such reduction, the gas plasma treatment described above should be applied to the coated devices as a pretreatment for gamma sterilization.

EXAMPLE 1

Preparation of the Reservoir Layer

A reservoir layer composition of heparin, silicone, and THF was prepared by the following method. An amount of a silicone-xylene mixture (~35% solid weight from Applied Silicone Corporation) was weighed. The solid silicone content was determined according to the vendor's analysis. Precalculated and weighed amounts of finely micronized heparin (2–6 microns) were added into the silicone to make a final coating of 37.5% by weight heparin. Then tetrahydrofuran (THF) HPLC grade (from Aldrich or EM Science) was added to the silicone and heparin in the amount of $V_{THF} = 25\ W_{silicone\ solid}$. Finally, a silane was added as a crosslinking agent. The solution was stirred with a stirring rod or magnet until the suspension was homogeneous.

Three Wallstent® self-expanding vascular stents were then spraycoated with the suspension. By adjusting the number of spray cycles, different coating thicknesses were placed upon the stents as shown in Table 1a. The coating thicknesses were measured using optical microscopy. After allowing the stents to rest at room temperature for about 30 minutes, the coated stents were moved to a convection oven and heated at 90° C. for 16 hours. Argon gas plasma treatment was applied to further cure the coating after the heat cure cycle. Each coated stent was thus cut in half to provide a total of six stent segments.

Preparation of the Outer Layer 10 mg/ml of TDMA-heparin/THF solution was prepared by dissolving a weighed amount of the TDMA-heparin powder into a beaker and adding THF solvent. The powder fully dissolved in the solvent in about 15 minutes. The outer layer composition was spray coated onto three of the stent segments, namely ND 815-1, 5, & 9 at, to produce outer layers of approximately 2 μm thick. The coated stents were air-dried. The remaining three stent segments, namely ND 815-1, 5, & 9 a, were not covered with an outer layer, and served as comparative examples.

Release Profile Based Upon Azure A Assay

To determine the heparin release profile of the coated stents, azure A assays were performed. About 2 cm of each coated stent was cut and placed into 100 ml of phosphate buffered saline and incubated in a shaker at 37° C. Periodic samplings of the solution were processed by complexing Azure A dye with the heparin to determine the amount of heparin released from the coatings into the sample solutions. At the time of sampling, the buffer was replaced with fresh saline.

Specifically 250 μl of each sample solution was diluted and pipetted into the wells of the 96-well microplate. 100 μl of Azure A dye solution of concentration 100 μg/ml (from Aldrich Chem. Co.) was pipetted into each sample well. The whole plate was then shaken and incubated at room temperature for exactly one hour. Absorbance of the solutions was then read at 505 nm using a micro plate reader. The concentrations of the samples were then determined by interpolation from a standard curve of solutions of known concentrations from 0 to 6.0 μg/ml in the increment of 0.6 μ/ml.

Table 1b summarizes the release rates of the stents at various times during an eight day period. This data has been compiled to generate the release profile of FIG. 1.

Results of Toluidine Blue Assay

To measure the concentration of heparin at the surface of the stents, a semi-quantitative toluidine blue assay was performed. About 1.5 cm of the stents were prepared and placed in small test tubes. 2 ml of the 100 μg/ml toluidine blue dye solution (from Aldrich) was added into the tubes. The test tubes were shaken gently and left under room conditions for exactly 30 minutes. The stents were then taken out of the dye and washed exhaustively with cold water. The surface of the stents were dried gently with paper towel. The stent samples were then transferred to another set of test tubes containing 2.00 ml of 1% sodium dodecyl sulfate solution and left under room conditions for minutes, prior to reading the absorbance of the solution at 640 nm in a UV spectrometer.

The dye uptaking results from the toluidine blue assay are presented in Table 1a. They show that the estimated concentrations of heparin present at the surfaces of the coated stents tended to be greater for the stents covered with the coatings of this invention as compared to stents covered only by a reservoir layer.

tubes were vortexed and incubated at 37° C. for exactly 5 minutes. 300 μl of a 20% acetic acid solution was added to stop the reaction. Absorbance of the chromophoric group was measured at 405 nm.

The antithrombin activity of the samples were calculated based on the standard curve of standard solutions of 0.1, 0.3, 0.5 and 0.7 IU/ml in heparin. It should be noted that the volumes of the reagents used for the test can be changed such that the ratio of the reagents are unchanged in order to obtain the absorbance of the testing solution within the range of the standard curve.

The results for the samples are presented in Table 1a. They show that the stents of the invention demonstrated significantly greater heparin or antithrombin activity and heparin surface concentrations than the stents which did not include a TDMA-heparin outer layer.

EXAMPLE 2

A mixture of heparin, silicone and THF was prepared by the following method. A silicone-xylene mixture (35% solid weight from Applied Silicone Corporation) was weighed. The solid silicone content was determined according to the vendor's analysis. Precalculated and weighed amounts of finely micronized heparin (2–6 microns) were added into the silicone to make a final coating of 37.5% heparin. Tetrahy- TABLE 1a

| Sample | nd815-5at | nd815-5a | nd815-9at | nd815-9a | nd815-1at | nd815-1a |
|---|---|---|---|---|---|---|
| Coating Composition | Reservoir layer with outer layer | Reservoir layer only | Reservoir layer with outer layer | Reservoir layer only | Reservoir layer with outer layer | Reservoir layer only |
| Thickness of Coating (μm) | 11 | 9 | 16 | 14 | 20 | 17 |
| Toluidine Blue Dye Uptake @ Day 8 (absorbance/cm$^2$) | 1.41 | 1.06 | 0.62 | 0.7 | 1.43 | 0.95 |
| FXa (mU/cm$^2$) @ Day 8 | 91 | 73.9 | 94.7 | 82 | 132.4 | 72.5 |

TABLE 1b

Release Rates (ug/cm$^2$/hr) Measured By Azure A Assay

| Time, days | nd815-1a | nd815-5a | nd815-9a | nd815-1at | nd815-5at | nd815-9at |
|---|---|---|---|---|---|---|
| 0.1 | 65 | 7.27 | 37.46 | 85.73 | 21.02 | 50 |
| 0.8 | 16.2 | 13.1 | 19.43 | 21.29 | 9.06 | 17 |
| 2.4 | 2.68 | 0.4 | 2.02 | 2.49 | 0.68 | 1.57 |
| 3.8 | 1.95 | 0 | 0 | 0.9 | 0 | 0.15 |
| 5.8 | 1.72 | 0 | 1.2 | 1 | 0 | 0.96 |
| 7.7 | 1.69 | 0.23 | 1.31 | 1.24 | 0.28 | 0.59 |

Results of Factor Xa Assay

To determine the pharmaceutical activity of the coated stent as well as the surface concentration of heparin a Factor Xa Assay was performed. About 0.5 cm of each stent sample was prepared and placed in a small test tube. 20 μl of antithrombin III at 1 IU/ml (from Helena Lab.) and 180 μl of 0.5 mol/l of tris buffer are added into the test tubes. The contents was shaken and incubated at 37° C. for about 10 minutes. Then 200 μl of Factor Xa, 71 nkat reagent (from Helena Lab.) was added into the test tubes. After about 1 minute, 200 μl of chromogenic substrate S 2765 1 mg/ml (Coatest, 82-14 13-39/5) was added into the tubes. The test drofuran (THF) HPLC grade (Aldrich or EM Science) was added until the solid content of silicone was 3.5%. Finally, crosslinking agent from the manufacturer was added into the suspension. The solution was stirred with a stirring rod or magnet until the suspension was homogeneous.

Wallstent® endoprostheses were then spraycoated with the suspension to achieve the reservoir coating thicknesses shown in Table 2a. Three coating series (e.g. A, B and C) were prepared as follows. After resting at room temperature for 30min., the coated stents designated as series A and C were moved to a convection oven and heated at 90° C. for 16 hours.

An outer layer composition was prepared by dissolving a weighed amount of TDMA-heparin powder into a beaker and adding THF to form a 10 mg/ml TDMA-heparin/THF solution. The powdered complex was fully dissolved in the solvent in about 15 minutes. Stent series A and B were spraycoated with this solution to form outer layers of the same thickness and allowed to air dry. The series B stents were heat cured at 90° C. for 16 hours.

The series C stents were then dip coated with the TDMA-heparin solution. The thickness of these outer layers is the same as that of the series A and B stents. Finally, argon gas plasma treatment was applied to further cure the coatings for all the series.

In summary, the three coating series were prepared as follows:

A: 1) spraycoated with a 37.5% heparin reservoir composition, 2) heat cured at 90° C. for 16 hours, 3) spraycoated with TDMA-heparin outer layer composition, and 4) exposed to argon gas plasma treatment.

B: 1) spraycoated with a 37.5% heparin reservoir composition, 2) spraycoated with TDMA-heparin outer layer composition, 3) heat cured at 90° C. for 16 hours, and 4) exposed to argon gas plasma treatment.

C: 1) spraycoated with a 37.5% heparin reservoir composition, 2) heat cured at 90° C. for 16 hours, 3) dip-coated with TDMA-heparin outer layer composition, and 4) exposed to argon gas plasma treatment.

The three assays described in Example 1 were performed for the stents. The results which are presented in Tables 2a and 2b show that the order of curing and means of applying the outer layer to the stent did not have significant effect on the activity or concentration of the heparin at the surface of the stent. However it should be noted that the stents of coating series B, in which the outer layer was exposed to heat curing showed improved surface morphology.

TABLE 2a

| Sample | A1-1 | A2-1 | B1-2 | B2-2 | C1-2 | C2-2 |
|---|---|---|---|---|---|---|
| Coatings Series | A | A | B | B | C | C |
| dye uptaking @ day 4 (absorbance/cm$^2$) | 1.18 | 1.46 | 1.84 | 1.7 | 1.22 | 1.39 |
| dye uptaking @ day 7 (absorbance/cm$^2$) | 0.66 | 0.42 | 0.82 | 1.28 | 0.93 | 0.63 |
| FXa (mU/cm$^2$) @ day 11 | 25.9 | 36.2 | 30 | 32.8 | 35.2 | 49.6 |
| coating thickness (um) | 5 | 23 | 6 | 11 | 5 | 16 |

TABLE 2b

Release Rate ($\mu$g/cm$^2$/hr)

| Time, days | A1-1 | A2-1 | B1-2 | B2-2 | C1-2 | C2-2 |
|---|---|---|---|---|---|---|
| 0.06 | 163.76 | 159.97 | 172.11 | 239.19 | 162.65 | 188.24 |
| 0.95 | 1.38 | 10.13 | 0.69 | 3.16 | 1.84 | 8.14 |
| 1.78 | 0.56 | 3.35 | 0.20 | 1.15 | 0.47 | 1.67 |
| 2.76 | 0.24 | 0.95 | 0.11 | 0.64 | 0.18 | 0.67 |
| 3.84 | 0.45 | 2.27 | 0.27 | 1.29 | 0.42 | 1.61 |
| 4.72 | 0.93 | 2.47 | 1.38 | 1.45 | 0.38 | 1.75 |
| 5.95 | 0.13 | 1.08 | 0.25 | 0.69 | 0.09 | 0.57 |
| 6.81 | 0.31 | 0.00 | 0.34 | 0.80 | 0.43 | 0.54 |

EXAMPLE 3

Wallstent® endoprostheses were spraycoated with the reservoir composition of Example 2 to achieve the coating thicknesses shown in Table 3a. An outer layer composition was prepared by weighing TDMA-heparin powder, placing it in a beaker, and adding THF to make the solution containing 10 mg/ml of TDMA-heparin in THF. The powder fully dissolved in the solvent in about 15 minutes. Four of the six sample stents were spraycoated with the TDMA-heparin solution to form outer layers of about 2 microns in thickness. All the samples were subjected to the toluidine blue assay and Azure A assay described above. Tables 3a and 3b detail the experimental results.

As shown in Table 3a, stents coated according to the invention (e.g. Sample TD1) exhibited greater heparin surface concentrations than stents having equal or thicker coatings comprised only of a reservoir layer (e.g. sample TD5).

TABLE 3a

| Sample | TD1 | TD2 | TD3 | TD4 | TD5 | TD6 |
|---|---|---|---|---|---|---|
| Coating Composition | Reservoir layer with outer layer | Reservoir layer with outer layer | Reservoir layer with outer layer | Reservoir layer with outer layer | Reservoir layer only | Reservoir layer only |
| coating thickness ($\mu$m) | 17 | 32 | 14 | 13 | 19 | 14 |
| dye uptaking @ day 5 (absorbance/cm$^2$) | 1.25 | 1.2 | 1.48 | 1.5 | 103 | 1.24 |
| dye uptaking @ day 7 (absorbance/cm$^2$) | 0.94 | 1.09 | 1.71 | 1.73 | 0.65 | 1.32 |
| dye uptaking @ day 9 (absorbance/cm$^2$) | 1.97 | 1.95 | 1.26 | 0.91 | 0.97 | 1.07 |

TABLE 3b

Release Data ($\mu$g/cm$^2$/hr)

| Time (days) | TD1 | TD2 | TD3 | TD4 | TD5 | TD6 |
|---|---|---|---|---|---|---|
| 0.08 | 630.94 | 672.89 | 368.70 | 342.80 | 162.94 | 146.52 |
| 1.73 | 5.01 | 5.33 | 4.30 | 3.61 | 6.87 | 3.52 |
| 4.73 | 2.53 | 2.90 | 1.87 | 1.83 | 2.60 | 3.19 |
| 7.02 | 3.20 | 3.26 | 3.14 | 2.87 | 4.02 | 3.61 |
| 8.90 | 0.50 | 0.62 | 0.08 | 0.00 | 0.98 | 0.78 |

EXAMPLE 4

Coated stents were prepared according to the method used to make the series B stents of Example 2 except that certain of the samples were not coated with an outer layer as indicated in Table 4a. Similar coating thicknesses of the reservoir layer and outer layer were maintained for the samples. These coated stents were sterilized by either gamma radiation or ethylene oxide. The samples were then subjected to toluidine blue assay and Azure A assay. Tables 4a and 4b detail the experimental results. These results show that sterilization of the coated stent, either by gamma radiation or ethylene oxide, does not adversely affect the heparin surface concentration in a significant manner.

TABLE 4a

| Samples | #2 | #3 | #15 | #19 | #16 |
|---|---|---|---|---|---|
| Sterilization Method | Gamma Radiation | Ethylene Oxide | None | Gamma Radiation | Ethylene Oxide |
| Coating Composition | Reservoir Layer Only | Reservoir Layer Only | Reservoir Layer with Outer Layer | Reservoir Layer with Outer Layer | Reservoir Layer with Outer Layer |
| Toluidine test @ day 3 (absorbance/cm$^2$) | 2.220 | 2.100 | 2.600 | 2.800 | 2.480 |
| Toluidine test @ day 6 (absorbance/cm$^2$) | 1.290 | 1.050 | 1.840 | 1.980 | 1.570 |
| Toluidine test @ day 10 (absorbance/cm$^2$) | 1.880 | 1.670 | 2.100 | 1.970 | 1.920 |

TABLE 4b

Release Data ($\mu$g/cm$^2$/hr)

| Time (days) | #2 | #3 | #15 | #19 | #16 |
|---|---|---|---|---|---|
| 0.08 | 138.30 | 215.88 | 283.40 | 212.25 | 232.46 |
| 1.01 | 4.28 | 11.55 | 6.80 | 5.59 | 9.53 |
| 1.99 | 1.99 | 3.02 | 2.29 | 1.66 | 3.16 |
| 3.06 | 1.96 | 1.78 | 1.78 | 1.71 | 1.99 |
| 3.93 | 1.61 | 1.41 | 1.40 | 1.12 | 1.46 |
| 4.88 | 1.73 | 0.82 | 1.12 | 1.18 | 1.13 |
| 5.84 | 2.37 | 0.84 | 1.20 | 1.25 | 1.46 |
| 6.74 | 1.17 | 0.53 | 0.59 | 0.58 | 0.80 |
| 7.86 | 1.30 | 0.65 | 1.31 | 0.85 | 1.11 |
| 8.74 | 0.90 | 0.34 | 0.96 | 0.35 | 1.27 |
| 9.84 | 0.78 | 0.24 | 1.25 | 0.59 | 1.26 |

EXAMPLE 5

Formation of Stabilized Coatings

To form the first layer of the coating, a silicone-xylene mixture (35% solid weight from Applied Silicone Corporation) was weighed and added to tetrahydrofuran (THF) HPLC grade (from Aldrich or EM Science). A crosslinking agent was added into the solution. The homogeneous solution was sprayed onto stents to form layers having thicknesses of 5 $\mu$m or less. The stents coated with the first layer of silicone were cured at 150° C. for 30 minutes. The stents were then treated with argon plasma for further curing.

Top layer compositions of silicone, THF and TDMA-heparin were prepared by dissolving the TDMA-heparin in the THF. The silicone-xylene mixture was added to the solution so that the solid silicone content was 3.5%. A crosslinking reagent was added to the solutions. The content of TDMA-heparin in the final solutions were 20% and 60% of the solid silicone.

The top layer compositions were sprayed onto the silicone coated stents. The thicknesses of the top layers of the samples as well as the amount of TDMA-heparin on the samples are given in Table 5a. The stents were then cured at 90° C. for 16 hours and then treated with argon plasma.

Release Experiments

After the coated stents were cut into 2 cm pieces, four pieces of each sample were placed into 100 mL of phosphate buffer solution (PBS). The buffer solution was changed daily and azure A assays were performed on the solution to determine the released heparin concentrations for the samples. The results are presented in Table 5b.

At the third, sixth and ninth days, a piece from each sample was used for toluidine blue dye uptaking assay. FXa assay was performed on the last piece of each sample on the ninth day to determine the heparin activity (See Table 5a for results).

TABLE 5a

| Sample | S1 | S2 | S3 | S4 |
|---|---|---|---|---|
| Thickness of Top Layer ($\mu$m) | 4 | 13 | 9 | 16 |
| Weight of TDMA-heparin (mg/cm$^2$) | 0.5000 | 2.1500 | 0.2300 | 0.6100 |
| Toluidine Blue Dye Uptake @ Day 3 (absorbance/cm$^2$) | 0.392 | 0.804 | 0.243 | 0.236 |
| Toluidine Blue Dye Uptake @ Day 6 (absorbance/cm$^2$) | 0.353 | 0.568 | 0.193 | 0.233 |
| Toluidine Blue Dye Uptake @ Day 9 (absorbance/cm$^2$) | 0.569 | 1.079 | 0.396 | 0.271 |
| FXa Activity (IU/cm$^2$) | 0.028 | 0.034 | 0.025 | 0.026 |

TABLE 5b

Release Rates ($\mu$g/cm$^2$/hr) Measured by Azure A Assay

| Time (days) | S1 | S2 | S3 | S4 |
|---|---|---|---|---|
| 0.08 | 2.720 | 3.902 | 2.912 | 4.831 |
| 0.92 | 0.190 | 0.313 | 0.273 | 0.336 |
| 2.17 | 0.105 | 0.042 | 0.053 | 0.087 |
| 3.08 | 0.060 | 0.000 | 0.000 | 0.019 |
| 4.00 | 0.164 | 0.032 | 0.031 | 0.048 |
| 4.98 | 0.000 | 0.000 | 0.000 | 0.000 |

EXAMPLE 6

Formation of Stabilized Coatings

The first layer of the coating was prepared and applied as in Example 5. In experiment series A, the coated stents were heat cured at 90° C. for 16 hours. In experiment series B, no heat treatment was applied.

A 10 mg/mL TDMA-heparin/THF top layer solution was prepared by dissolving the TDMA-heparin in the THF. The stents were sprayed coated with top layer solution and then air dried. The amount of TDMA-heparin applied to each sample stent is provided in Table 6a. The coated stents of series B were then heat treated in a convection oven at 90° C. for 16 hours. Both series of stents were treated with argon plasma.

In summary, the two coating series were prepared as follows:

A: 1) spraycoated with silicone first layer solution, 2) heat cured, 3) spraycoated with TDMA-heparin top layer composition, and 4) argon plasma treated.

B: 1) spraycoated with silicone first layer solution, 2) spraycoated with TDMA-heparin top layer composition, 3) heat cured and 4) argon plasma treated.

Release Experiments

Four 2 cm pieces of coated stents from each sample of each series were placed into 100 mL of phosphate buffer solution (PBS) having a pH of 7.4. Another 4 pieces from each series were placed into 100 mL of polyethylene glycol (PEG)/water solution (40/60 v/v, MW of PEG=400). The stent pieces were incubated at 37° C. in a shaker. The buffer and PEG solutions were changed daily and azure A assays were performed on the solution to determine the released heparin concentrations. The results are presented in Table 6b.

On the third, sixth and eleventh days, a piece from each sample was used for toluidine blue dye uptaking assay (See Table 5a for results). FXa assay was performed on the last piece of each sample to determine the heparin activity. It was found that the heparin activity was too high to be quantified by a FXa assay.

Release of heparin in plasma was also studied. 1 cm pieces of a coated stent from series B was put into 1 mL of citrated human plasma (from Helena Labs.), which was in lyophilized form and was reconstituted by adding 1 mL of sterile deionized water. Three sets of stent plasma solutions were incubated at 37° C. and the plasma was changed daily. In a separate study, it was found that citrated human plasma was stable at 37° C. for 24 hours (activated partial thromboplastin time test). Toluidine blue assay was performed for the stent incubated in the plasma for one day and for seven days. The one day dye uptaking showed no loss activity; the dye uptaking at 7 days showed a 40% loss of activity. Also, FXa assay was performed on day 7. The antithrombin activity was higher than the quantification limit (>64 mU/cm$^2$).

TABLE 6a

| Experimental Series | B | B | B | A | A | A |
|---|---|---|---|---|---|---|
| Sample | T1 | T2 | T3 | T4 | T5 | T6 |
| Weight of TDMA-heparin (mg/cm$^2$) | 0.4200 | 0.5100 | 0.5300 | 0.3300 | 0.6300 | 0.3900 |
| Eluting media | PBS | PBS | PEG/water | PBS | PBS | PEG/water |
| Toluidine Blue Dye Uptake @ Day 3 (absorbance/cm$^2$) | 0.927 | 0.961 | 0.673 | 0.816 | 1.363 | 0.744 |
| Toluidine Blue Dye Uptake @ Day 6 (absorbance/cm$^2$) | 1.655 | 1.104 | 0.983 | 1.163 | 1.951 | 1.278 |
| Toluidine Blue Dye Uptake @ Day 11 (absorbance/cm$^2$) | 1.345 | 1.527 | 1.424 | 1.114 | 2.210 | 1.277 |

TABLE 6b

Release Rates ($\mu$g/cm$^2$/hr) Measured by Azure A Assay

| Time (days) | T1 | T2 | T3 | T4 | T5 | T6 |
|---|---|---|---|---|---|---|
| 0.08 | 1.53 | 1.31 | 1.55 | 0.00 | 0.00 | 1.08 |
| 1.00 | 0.05 | 0.05 | 0.97 | 0.00 | 0.01 | 0.39 |
| 2.02 | 0.00 | 0.00 | 0.19 | 0.00 | 0.06 | 0.11 |
| 2.97 | 0.20 | 0.00 | 0.12 | 0.00 | 0.32 | 0.11 |
| 4.04 | 0.00 | 0.00 | 0.06 | 0.00 | 0.13 | 0.00 |
| 4.88 | 0.00 | 0.00 | 0.03 | 0.00 | 0.35 | 0.00 |

EXAMPLE 7

To examine the effect of the curing order and the argon plasma treatment on the binding effect of TDMA-heparin on silicone surfaces, the following samples were prepared. 5.0 mm Elgiloy stents were coated with silicone having a coating weight of 13.5 mg/cm$^2$. A top layer solution of 10 mg/ml of TDMA-heparin/THF was sprayed onto the stents. The coating weight of the top layer was about 0.4 mg/cm$^2$. The heating and argon plasma treatment steps were applied to the stents as described below. The stents were heat cured at 90° C. for 16 hours.

TE1: 1) spraycoated with silicone solution, 2) heat cured, 3) spraycoated with TDMA-heparin top layer solution, and 4) argon plasma treated.

TE2: 1) spraycoated with silicone solution, 2) heat cured and 3) spraycoated with TDMA-heparin top layer solution.

TE3: 1) spraycoated with silicone solution, 2) spraycoated with TDMA-heparin top layer solution 3) heat cured and 4) argon plasma treated.

TE4: 1) spraycoated with silicone solution, 2) spraycoated with TDMA-heparin top layer solution and 3) heat cured.

The release study was performed in PBS buffer at 37° C. The results, which are listed in Table 7, show that the combined curing of the coating with both heat treatment and argon gas treatment increases the binding efficacy of the TDMA-heparin on the device and consequently prolongs the heparin activity.

TABLE 7

| Sample | TE1 | TE2 | TE3 | TE4 |
|---|---|---|---|---|
| Coating Process | Si/heat/TDMA-hep/plasma | Si/heat/TDMA-hep | Si/TDMA-hep/heat/plasma | Si/TDMA-hep/heat |
| Toluidine Blue Dye Uptaking @ Day 2.02 (absorbance/cm$^2$) | 0.881 | 0.844 | 1.287 | 1.095 |
| Toluidine Blue Dye Uptaking @ Day 6.05 (absorbance/cm$^2$) | 0.985 | 0.705 | 1.336 | 1.055 |
| Toluidine Blue Dye Uptaking @ Day 8.6 (absorbance/cm$^2$) | 0.715 | 0.691 | 1.310 | 1.009 |

EXAMPLE 8

To further compare the binding efficacy of coatings exposed to both heat and plasma treatment and that of coatings which are only heat treated, the following samples were prepared. The thicknesses of both the silicone layer and top layer were kept constant at 3 mg/cm$^2$ and 0.5 mg/cm$^2$, respectively.

ND-1:
1) spraycoated with silicone solution,
2) heat cured at 150° C. for 45 minutes,
3) spraycoated with TDMA-heparin top layer solution, and
4) heat cured at 90° C. for 16 hours.

ND-1P:
same as ND-1 but further treated with argon plasma.

ND-2:
1) spraycoated with silicone solution,
2) spraycoated with TDMA-heparin top layer solution, and
3) heat cured at 90° C. for 16 hours.

ND-2P:
same as ND-2 but further treated with argon plasma.

ND-3:
1) spraycoated with silicone solution,
2) heat cured at 150° C. for 60 minutes, and
3) spraycoated with TDMA-heparin top layer solution.

ND-3P:
same as ND-3 but further treated with argon plasma.

The release study was performed in citrate bovine plasma (CBP). The stents were cut into 1.5 cm pieces and placed into a sterilized plastic vial containing 4 ml of CBP at 37° C. The plasma was changed daily. From the third day, 1 ml of CBP was used instead. Toluidine blue assay and FXa assay were performed after 7 days of eluting. The results presented in Table 8 confirm the finding of Example 7, that plasma treatment enhances the binding of the TDMA-heparin to the stents.

TABLE 8

| Sample | ND-1 | ND-1P | ND-2 | ND-2P | ND-3 | ND-3P |
|---|---|---|---|---|---|---|
| Argon Plasma Treatment | NO | YES | NO | YES | NO | YES |
| Toluidine Blue Dye Uptaking (absorbance/cm$^2$) | 0.683 | 0.577 | 0.743 | 0.805 | 0.696 | 0.854 |
| FXA activity (mIU/cm$^2$) | 0 | 1.4 | 2.7 | 9.0 | 0 | 5.0 |

The description contained herein is for purposes of illustration and not for purposes of limitation. Changes and modifications may be made to the embodiments of the description and still be within the scope of the invention. Furthermore, obvious changes, modifications or variations will occur to those skilled in the art. Also, all references cited above are incorporated herein, in their entirety, for all purposes related to this disclosure.

We claim:

1. A medical device having at least a portion which is insertable or implantable into the body of a patient, wherein the portion has a surface which is adapted for exposure to body tissue of the patient and wherein at least a part of the surface is covered with a coating for release of at least one biologically active material, the coating comprising an internal reservoir layer and an outer layer in contact with the reservoir layer;

wherein the outer layer comprises an ionic surfactant complexed to the biologically active material; and wherein the reservoir layer comprises a polymer incorporating the biologically active material which is substantially free of any ionic surfactant such that the biologically active material of the reservoir layer can migrate outwardly from the reservoir layer, and at least some of the biologically active material of the reservoir can complex with the ionic surfactant in the outer layer as the biologically active material releases from the outer layer.

2. The device of claim 1 wherein the device is an expandable stent.

3. The device of claim 2 wherein the device is a self-expanding stent.

4. The device of claim 1 wherein the polymer of the reservoir layer is an elastomeric material.

5. The device of claim 4 wherein the polymer of the reservoir layer is selected from the group consisting of silicones, polyurethanes, thermoplastic elastomers, ethylene vinyl acetate copolymers, polyolefin elastomers, and EPDM rubbers.

6. The device of claim 5 wherein the polymer of the reservoir layer is silicone.

7. The device of claim 1 wherein the biologically active material of the reservoir layer is in a particulate form having an average particle size of 1 to 100 microns.

8. The device of claim 7 wherein the ratio of reservoir layer thickness to average particle diameter is greater than about 3.

9. The device of claim 7 wherein the ratio of reservoir layer thickness to average particle diameter is greater than about 5.

10. The device of claim 1 wherein the biologically active material is selected from the group consisting of glucocorticoids, heparin, hirudin, angiopeptin, aspirin, ACE inhibitors, growth factors, oligonucleotides, antiplatelet agents, anti-hypertensives, anti-coagulant agents, antimitotic agents, antioxidants, antimetabolite agents, anti-inflammatory agents and antibiotics.

11. The device of claim 10 wherein the biologically active material is heparin.

12. The device of claim 1 wherein the reservoir layer comprises about 0.1 to about 90 weight % of the biologically active material.

13. The device of claim 12 wherein the reservoir layer comprises about 10 to about 45 weight % of the biologically active material.

14. The device of claim 1 wherein the reservoir layer is about 5 to about 200 microns thick.

15. The device of claim 14 wherein the reservoir layer is about 15 to about 50 microns thick.

16. The device of claim 1 wherein the ionic surfactant of the outer layer is a quaternary ammonium complex.

17. The device of claim 16 wherein the ionic surfactant comprises a tridodecylmethylammonium ion.

18. The device of claim 1 wherein the outer layer is about 0.1 to about 10 microns thick.

19. The device of claim 1 wherein the coating is constructed to maintain biologically active material on the surface of the device for at least about 24 hours.

* * * * *

UNITED STATES PATENT AND TRADEMARK OFFICE
CERTIFICATE OF CORRECTION

PATENT NO. : 5,879,697

DATED : March 9, 1999

INVENTOR(S) : Ni Ding, Jennifer E. Raeder-Devens and Tuyethoa Thi Trinh

It is certified that error appears in the above-identified patent and that said Letters Patent is hereby corrected as shown below:

On the cover of the patent, under "Inventors [76]", Jennifer E. Raeder-Devens and Tuyethoa Thi Trinh should be deleted as inventors.

On the cover of the patent, Schneider (USA) Inc, Plymouth, MN should appear as the assignee.

Signed and Sealed this

Twenty-fourth Day of August, 1999

Attest:

Q. TODD DICKINSON

*Attesting Officer*     *Acting Commissioner of Patents and Trademarks*